United States Patent
Wang et al.

(10) Patent No.: US 12,113,177 B2
(45) Date of Patent: Oct. 8, 2024

(54) LITHIUM OXYHALIDE ELECTROCHEMICAL CELL DESIGN FOR HIGH-RATE DISCHARGE

(71) Applicant: Electrochem Solutions Inc., Clarence, NY (US)

(72) Inventors: Yufei Wang, Easton, MA (US); John S. Miller, Dedham, MA (US); John Hession, Braintree, MA (US); Arden P Johnson, Arlington, MA (US)

(73) Assignee: Electrochem Solutions, Inc., Clarence, NY (US)

( * ) Notice: Subject to any disclaimer, the term of this patent is extended or adjusted under 35 U.S.C. 154(b) by 0 days.

(21) Appl. No.: 18/225,960

(22) Filed: Jul. 25, 2023

(65) Prior Publication Data
US 2023/0365550 A1      Nov. 16, 2023

Related U.S. Application Data

(63) Continuation of application No. 16/925,755, filed on Jul. 10, 2020, now Pat. No. 11,923,511.
(Continued)

(51) Int. Cl.
*H01M 10/0587* (2010.01)
*A61K 31/433* (2006.01)
(Continued)

(52) U.S. Cl.
CPC ....... *H01M 10/0587* (2013.01); *A61K 31/433* (2013.01); *A61K 31/44* (2013.01);
(Continued)

(58) Field of Classification Search
CPC ........... H01M 10/0587; H01M 50/186; H01M 50/116; H01M 50/1535; H01M 50/183;
(Continued)

(56) References Cited

U.S. PATENT DOCUMENTS

| | | | |
|---|---|---|---|
| 4,042,756 | A | 8/1977 | Goebel et al. |
| 5,882,815 | A | 3/1999 | Tagawa |

(Continued)

OTHER PUBLICATIONS

"In re Ruff, 256 F.2d 590, 118 USPQ 340 (CCPA 1958)."
Marincic, Nikola , "Lithium Batteries with Liquid Depolarizers (From: Modern Aspects of Electrochemstry, No. 15)."

*Primary Examiner* — Brian R Ohara
*Assistant Examiner* — Emily Elizabeth Freeman
(74) *Attorney, Agent, or Firm* — Michael F. Scalise

(57) ABSTRACT

A novel wound electrode assembly for a lithium oxyhalide electrochemical cell is described. The electrode assembly comprises an elongate cathode of an electrochemically non-active but electrically conductive carbonaceous material disposed between an inner elongate portion and an outer elongate portion of a unitary lithium anode. That way, lithium faces the entire length of the opposed major sides of the cathode. This inner anode portion/cathode/outer anode portion configuration is rolled into a wound-shaped electrode assembly that is housed inside a cylindrically-shaped casing. A cylindrically-shaped sheet-type spring centered in the electrode assembly presses outwardly to limit axial movement of the electrode assembly. In one embodiment, all the non-active components, except for the cathode current collector, which is nickel, are made of stainless-steel. This provides the cell with a low magnetic signature without adversely affecting the cell's high-rate capability.

22 Claims, 4 Drawing Sheets

Related U.S. Application Data

(60) Provisional application No. 62/873,387, filed on Jul. 12, 2019.

(51) Int. Cl.

| | |
|---|---|
| *A61K 31/44* | (2006.01) |
| *A61K 31/4439* | (2006.01) |
| *A61K 31/444* | (2006.01) |
| *A61K 31/4545* | (2006.01) |
| *A61K 31/4965* | (2006.01) |
| *A61K 31/497* | (2006.01) |
| *A61K 31/501* | (2006.01) |
| *A61K 31/505* | (2006.01) |
| *A61K 31/506* | (2006.01) |
| *A61K 45/06* | (2006.01) |
| *C07D 213/75* | (2006.01) |
| *C07D 239/42* | (2006.01) |
| *C07D 241/20* | (2006.01) |
| *C07D 285/135* | (2006.01) |
| *C07D 401/04* | (2006.01) |
| *C07D 401/12* | (2006.01) |
| *C07D 417/06* | (2006.01) |
| *C07D 417/08* | (2006.01) |
| *C07D 417/14* | (2006.01) |
| *H01M 4/134* | (2010.01) |
| *H01M 4/36* | (2006.01) |
| *H01M 4/38* | (2006.01) |
| *H01M 4/58* | (2010.01) |
| *H01M 4/62* | (2006.01) |
| *H01M 4/66* | (2006.01) |
| *H01M 10/052* | (2010.01) |
| *H01M 10/0568* | (2010.01) |
| *H01M 10/0569* | (2010.01) |
| *H01M 50/119* | (2021.01) |
| *H01M 50/131* | (2021.01) |
| *H01M 50/138* | (2021.01) |
| *H01M 50/148* | (2021.01) |
| *H01M 50/159* | (2021.01) |
| *H01M 50/186* | (2021.01) |
| *H01M 50/188* | (2021.01) |
| *H01M 50/191* | (2021.01) |
| *H01M 50/466* | (2021.01) |

(52) U.S. Cl.
CPC ........ *A61K 31/4439* (2013.01); *A61K 31/444* (2013.01); *A61K 31/4545* (2013.01); *A61K 31/4965* (2013.01); *A61K 31/497* (2013.01); *A61K 31/501* (2013.01); *A61K 31/505* (2013.01); *A61K 31/506* (2013.01); *A61K 45/06* (2013.01); *C07D 213/75* (2013.01); *C07D 239/42* (2013.01); *C07D 241/20* (2013.01); *C07D 285/135* (2013.01); *C07D 401/04* (2013.01); *C07D 401/12* (2013.01); *C07D 417/06* (2013.01); *C07D 417/08* (2013.01); *C07D 417/14* (2013.01); *H01M 4/134* (2013.01); *H01M 4/368* (2013.01); *H01M 4/382* (2013.01); *H01M 4/582* (2013.01); *H01M 4/623* (2013.01); *H01M 4/625* (2013.01); *H01M 4/662* (2013.01); *H01M 10/052* (2013.01); *H01M 10/0568* (2013.01); *H01M 10/0569* (2013.01); *H01M 50/119* (2021.01); *H01M 50/138* (2021.01); *H01M 50/1535* (2021.01); *H01M 50/159* (2021.01); *H01M 50/186* (2021.01); *H01M 50/188* (2021.01); *H01M 50/191* (2021.01); *H01M 50/466* (2021.01); *H01M 50/131* (2021.01); *H01M 2300/0031* (2013.01); *Y02A 50/30* (2018.01)

(58) Field of Classification Search
CPC ............. H01M 50/191; H01M 50/155; H01M 50/138; H01M 4/134; H01M 4/368; H01M 4/382; H01M 4/582; H01M 4/623; H01M 4/625; H01M 4/662; H01M 10/052; H01M 10/0568; H01M 10/0569; H01M 50/131; H01M 2300/0031
See application file for complete search history.

(56) References Cited

U.S. PATENT DOCUMENTS

| | | |
|---|---|---|
| 6,593,028 B1 | 7/2003 | McCormick |
| 2002/0132167 A1 | 9/2002 | Gan et al. |
| 2002/0155350 A1 | 10/2002 | Spillman |
| 2011/0016706 A1 | 1/2011 | Jan et al. |
| 2011/0052985 A1 | 3/2011 | Kashiwazaki et al. |
| 2018/0090756 A1 | 3/2018 | Yoo et al. |
| 2018/0316054 A1 | 11/2018 | Matsushita et al. |
| 2020/0044225 A1* | 2/2020 | Eo .......... H01M 10/04 |
| 2020/0350537 A1 | 11/2020 | Uto |

* cited by examiner

LITHIUM OXYHALIDE ELECTROCHEMICAL CELL DESIGN FOR HIGH-RATE DISCHARGE

CROSS-REFERENCE TO RELATED APPLICATIONS

This application is a continuation of U.S. application Ser. No. 16/925,755, filed on Jul. 10, 2020, now U.S. Pat. No. 11.923,511, which claims priority to U.S. provisional application Ser. No. 62/873,387, filed on Jul. 12, 2019.

BACKGROUND OF THE INVENTION

1. Field of the Invention

The present invention relates to the art of electrochemical cells, and more particularly, to high-rate lithium oxyhalide electrochemical cells. Lithium oxyhalide electrochemical cells of the present invention have a novel wound electrode assembly design for sustained high-rate discharge, even when the cells are subjected to high shock and vibration conditions, such as typically occurs in downhole drilling and testing applications, and the like.

2. Prior Art

The most widely-used design for a lithium oxyhalide electrochemical cell intended for use in downhole drilling and testing applications is the "moderate-rate" design. In the moderate-rate design, the cathode is a flat, relatively thick plate. A layer of lithium is wrapped around the cathode, covering both of its opposed outer major surfaces. This anode/cathode electrode assembly is then rolled into a horseshoe shape and inserted into a cell casing, preferably a cylindrically-shaped casing.

Two features make the moderate-rate design a mechanically strong structure for a lithium oxyhalide electrochemical cell. First, an anode current collector tab along the upper edge of the outer side of the anode is securely welded to substantially the entire inner circumference of the cell casing, thus immobilizing the electrode assembly. Second, a sheet-type stainless-steel spring is wound into a cylinder and inserted into the center of the electrode assembly. The spring presses outwardly against the electrodes, further limiting any possible axial movement of the electrode assembly with respect to the cylindrical casing. These features make the moderate-rate design for a lithium oxyhalide electrochemical cell extremely rugged and capable of withstanding the rigorous shock and vibration conditions that are typically encountered in downhole drilling and testing applications, and the like. Unfortunately, the surface area of the electrodes limits the ability of moderate-rate lithium oxyhalide cells to deliver the relatively high levels of current that are demanded in today's downhole market.

Thus, to increase the current capability of a lithium oxyhalide electrochemical cell intended for downhole applications, and the like, it is necessary to increase the surface area of the electrode assembly. The most common design approach for increasing electrode surface area is to use long flat electrodes. One layer of anode and one layer of cathode is placed together and wound into a spiral-wound or so-called "jelly-roll" arrangement. The jelly-roll electrode assembly is then inserted into the cell casing. This is known as a spiral-wound design.

Spiral-wound electrode arrangements are typically assembled by winding the anode and cathode and intermediate separator together around a mandrel. After the jelly-roll electrode assembly is removed from the mandrel, a center hole remains in the wound structure where the mandrel was. This hole is potentially a location where a spring can be inserted to apply an outwardly biasing pressure to the electrode assembly. However, this is seldom done. That is because the central hole is usually minimized to maximize the amount of anode and cathode materials that are inserted into the cell casing.

In a spiral-wound arrangement, each of the anode and cathode face the opposite electrode on both sides across a layer of separator over most of the electrode assembly length. However, the outermost layer of electrode that is adjacent to the casing wall, typically the anode in a case-negative design, faces the opposite electrode, typically the cathode, only on one side. The other side of the outermost electrode faces the inactive casing wall. To ensure efficient utilization of the anode active material and cathode material, it is necessary that the outermost electrode be reduced in thickness along the section that faces the casing wall. That is so there will not be excess anode active material that cannot be discharged and is therefore wasted.

There are various ways of reducing the thickness of that section of the outermost electrode, but the need to do this makes the cell design and the manufacturing processes more complicated. The section of electrode with reduced thickness may also end up mechanically weaker than the rest of the electrode because adhesion to the current collector is reduced. Electrode designs in which both electrodes have a constant thickness along their full length are greatly preferred both for ease of manufacturing and for mechanical stability.

Another fundamental problem with spiral-wound designs for high shock and vibration environments is that the electrodes tend to move relative to each other. This movement can cause the anode and cathode to slip or fall out of alignment, leading to a serious risk of internal shorting. In severe cases of misalignment, the center of the jelly-roll is significantly displaced relative to the outermost winds. This phenomenon is called "telescoping." Telescoped electrodes can extend above the protective edges of the separator material that is between the opposite polarity electrodes, possibly leading to an anode-to-cathode short circuit, or direct contact between an electrode and an electrically conductive surface of the cell casing or lid.

Various methods have been used to immobilize the wound electrodes in spiral-wound designs. One method is simply to use electrodes that come very close to filling the entire length of the cylindrically-shaped casing so that there is little room available for the electrodes to move back and forth within the cylinder. This approach is risky because the edges of the electrodes are very close to the bottom wall and upper lid of the casing, and mechanically strong electrically insulating material must be present at the upper and lower ends of the electrode assembly to prevent electrical contact with the casing. Designs like this also risk having inadequate void space, which must be available in a casing to allow for expansion of the electrolyte when the cell is heated during close welding of the lid to the cylindrically-shaped casing container and when closing the electrolyte fill port in the lid.

Another approach is to position a mechanically rigid spacer at the upper end of the electrode assembly but below the casing lid. A gap is left between the lid and the upper edge of the spacer. The spacer restricts movement of the electrodes while a hole in the upper spacer allows electrolyte to expand into the void space above the spacer as the temperature changes during the lid welding and electrolyte fill port closure operations. However, not only does this cell construction still require mechanically strong electrical insulation at the opposite ends of the electrode assembly, attaching the upper spacer inside the cylindrically-shaped casing container, but below the upper edge of the container, is relatively difficult. That is because the spacer must be inserted into the casing container, be properly positioned, and then welded in place or otherwise immobilized. These are time consuming steps that add cost to cell manufacture.

A third design approach for ruggedizing a spirally-wound or jelly-roll type lithium oxyhalide electrode assembly is to include additional current collector tabs. A non-ruggedized design usually includes only one tab per current collector to conduct current from the electrode to an external contact. In a ruggedized design, the number of tabs is increased to two, three or more per electrode. These additional tabs are spaced along the length of the electrode to increase the mechanical strength at several locations along the electrode. This reduces the risk of telescoping that would occur if one end of the anode or cathode were to move more than the other electrode. One disadvantage of this type of design, however, is the increased complexity of the assembly operations as the additional current collector tabs must be welded to the appropriate electrical contacts. Another disadvantage is that the tabs take up space in the electrode assembly, reducing space that would otherwise be available for active materials.

SUMMARY OF THE INVENTION

Accordingly, one requirement for a lithium oxyhalide electrochemical cell according to the present invention is that the cell is capable of consistently delivering high-current pulses during which the discharge voltage remains relatively high while the cell delivers as close to 100% of its theoretical capacity as possible. The lithium oxyhalide cell must also be rugged enough to withstand relatively high levels of shock and vibration and possibly have a relatively low magnetic signature.

These requirements are achieved using three key design features, which will be described in detail hereinafter. The novel design features for a lithium oxyhalide electrochemical cell according to the present invention are: 1) an electrode assembly construction that provides high-rate capability with a rugged structure; 2) a balance of non-active components (other than the anode active material and cathode material) that provide a relatively low magnetic signature without compromising high electrical conductivity; and 3) a new electrolyte formulation that provides both high-rate pulsing capability and high capacity.

These and other objects of the present invention will become increasingly more apparent to those skilled in the art by reference to the following detailed description and to the appended drawings.

DETAILED DESCRIPTION OF THE PREFERRED EMBODIMENTS

As used herein, the term "pulse" means a short burst of electrical current of significantly greater amplitude than that of a pre-pulse current immediately prior to the pulse. A pulse train consists of at least two pulses of electrical current delivered in relatively short succession with or without open circuit rest between the pulses. An exemplary pulse train may consist of a one-second pulse (50 mA/cm$^2$) alternating with a lower background current (2 mA/cm$^2$) for two minutes, with this sequence repeated indefinitely during operation of the downhole drilling or testing tool. A typically used range of current densities for cells powering downhole drilling or testing tools is from about 0.1 mA/cm$^2$ to about 100 mA/cm$^2$, and more preferably from about 1 mA/cm$^2$ to about 50 mA/cm$^2$. Typically, a pulse that is suitable for downhole drilling and testing applications may extend from milliseconds (ms) to several seconds or minutes. However, it could be significantly shorter or longer depending on the specific cell design and chemistry.

As defined herein, "non-active" means that the material does not undergo an electrochemical reaction within an electrochemical cell. For example, acetylene black is non-active within an oxyhalide cell as it does not chemically react with the liquid oxyhalide catholyte. The term "active" means that the material undergoes an electrochemical reaction within an electrochemical cell. The term "catholyte" means an ionically conductive solution that is operatively associated with the anode and the cathode.

Figure 1:
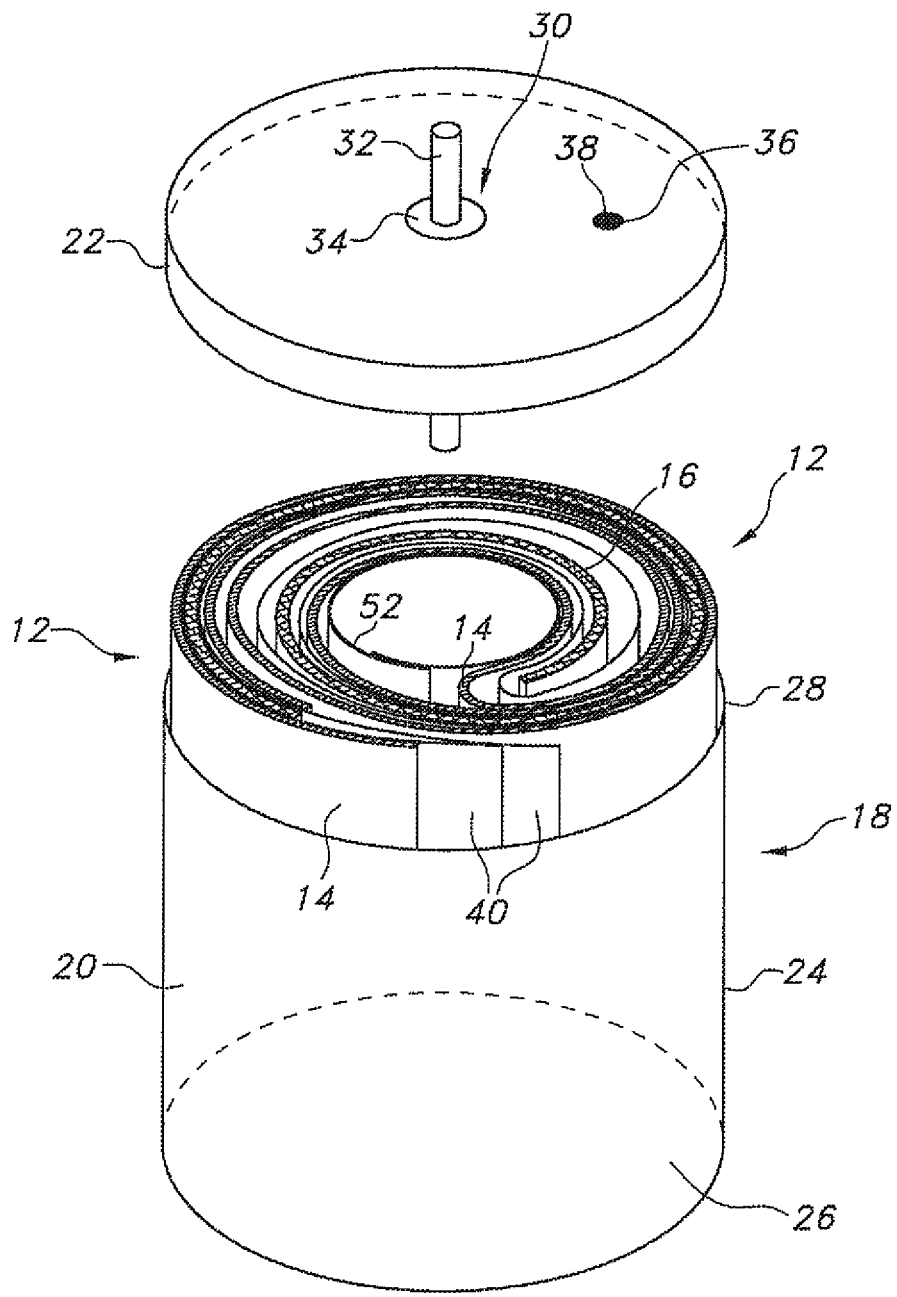
FIG. 1 is a perspective view of a lithium oxyhalide electrochemical cell 10 according to the present invention

Turning now to the drawings, FIG. 1 is a perspective view of a lithium oxyhalide electrochemical cell 10 according to the present invention. The cell 10 comprises an electrode assembly 12 of an elongate anode 14 wound with an elongate cathode 16 (FIG. 2) housed inside a casing 18. The casing 18 is typically of stainless-steel and comprises an open-ended container 20 closed by a stainless-steel lid 22. The container 20 has a cylindrically-shaped sidewall 24 extending from a closed bottom wall 26 to an upper edge 28. The upper edge 28 surrounds an open upper end that provides access to the interior of the container 20. After the electrode assembly 12 of the present lithium oxyhalide cell 10 is manufactured, it is moved into the container 20 through the open upper end. With the electrode assembly 12 housed inside the container 20, the open upper end is closed by welding the lid 22 to the upper edge 28 thereof.

The lid 22 supports a glass-to-metal seal 30 comprising a terminal pin 32 surrounded by an insulating glass 34. The insulating glass 34 electrically isolates the terminal pin 32 from the rest of the casing 18 comprising the container 20 and the closure lid 22. In a case-negative cell design, the anode 14 is electrically connected to the casing 18 and the terminal pin 32 is electrically connected to the cathode 16.

A fill port 36 is provided in the lid 22. A catholyte (not shown), which will be described in greater detail hereinafter, is filled into the casing 18 through the fill port 36 to activate the electrode assembly 12. A closure member 38, such as a stainless-steel ball, is then welded into the fill port 36 to hermetically seal the casing 18.

Figure 2:
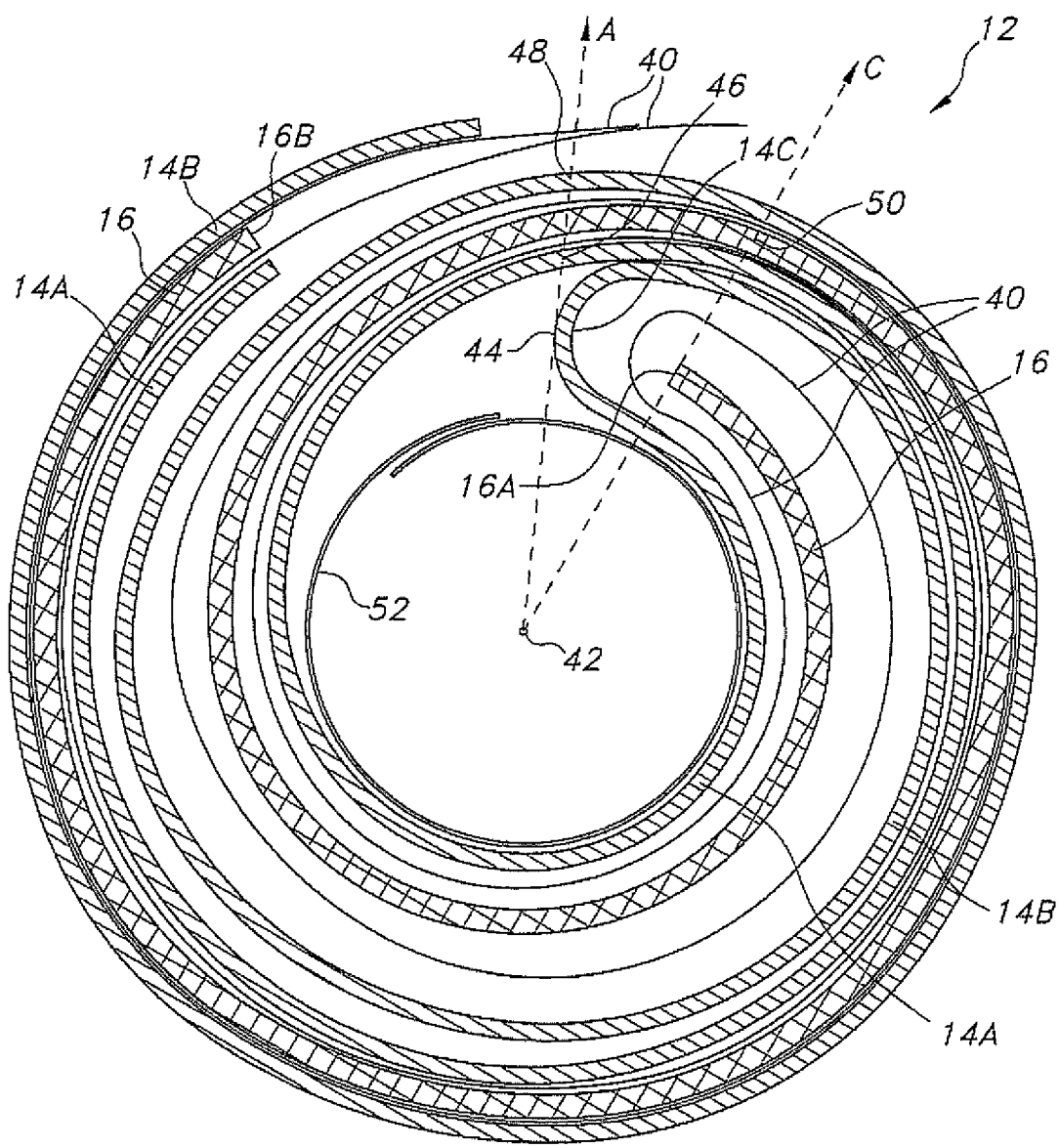
FIG. 2 is a plan view of the electrode assembly 12 of the electrochemical cell 10 shown in FIG. 1.

FIG. 2 is an enlarged plan view of the electrode assembly 12 shown in FIG. 1. The electrode assembly 12 comprises the elongate plate-shaped cathode 16 contained in an envelope of separator material 40. The separator 40 prevents direct physical contact of the anode 14 with the elongate, plate-shaped cathode 16.

Figure 3:
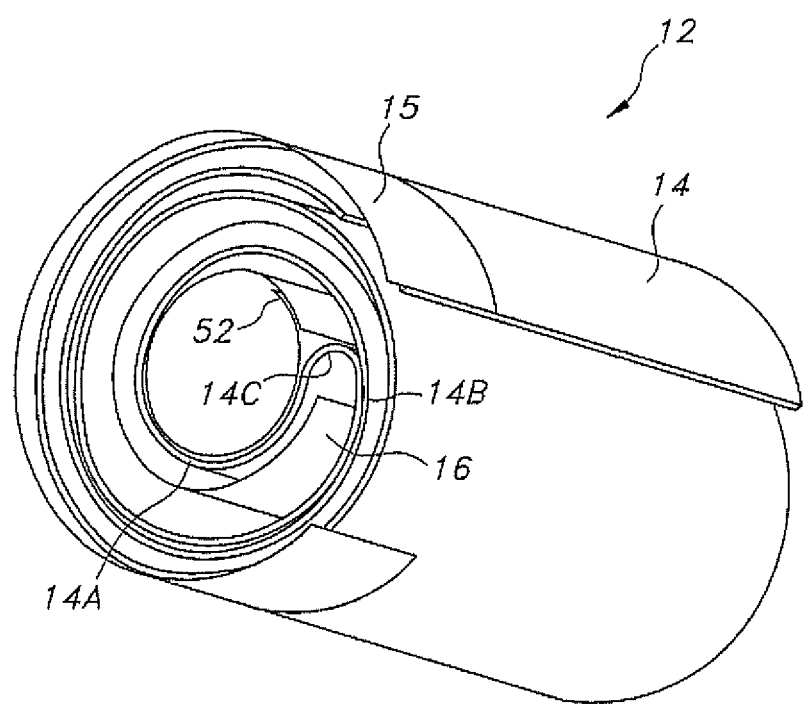
FIG. 3 is a perspective view of the electrode assembly 12 with an anode current collector tab 15 extending from an outer portion of the anode 14.
Figure 4:
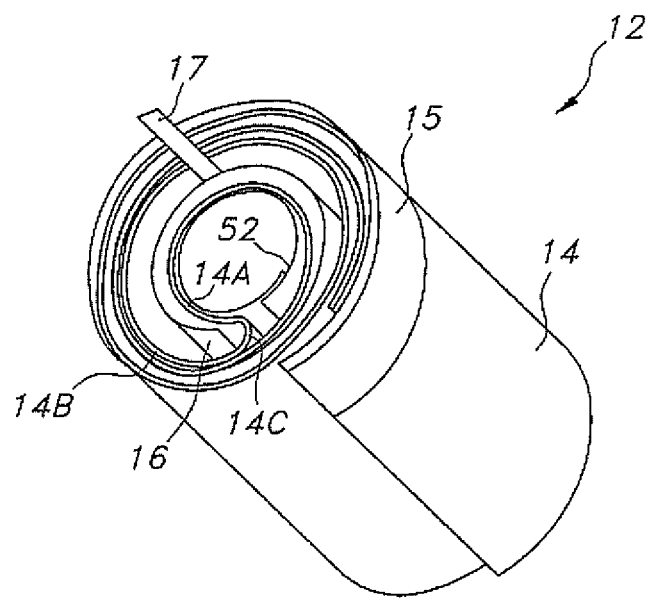
FIG. 4 is a perspective view of the electrode assembly 12 illustrating the anode current collector tab 15 shown in FIG. 3 and a cathode current collector tab 17 extending from the cathode 16.
Figure 5:
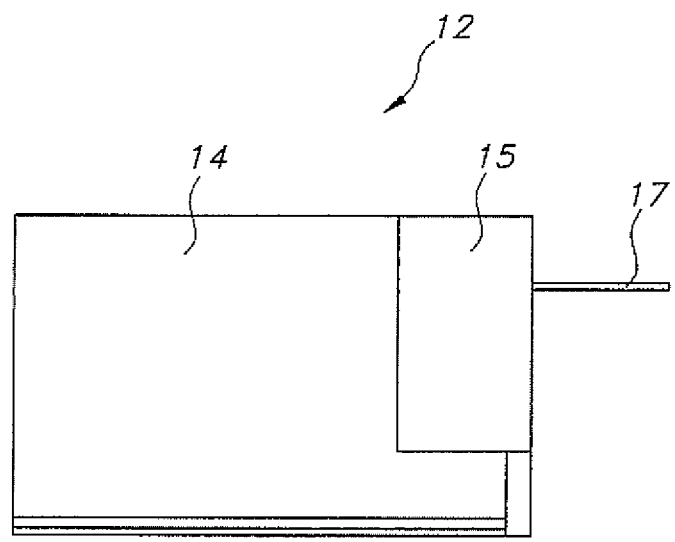
FIG. 5 is a side elevational view of the electrode assembly 12 illustrated in FIG. 4 showing both the anode current collector tab 15 and the cathode current collector tab 17.

The anode 14 is comprised of two sheets or foils of anode active material, preferably lithium, that are contacted by pressing or rolling onto the opposed major sides of an electrically conductive anode current collector (not shown), preferably comprising stainless-steel. The anode current collector is preferably a screen-type member having a plurality of perforations or openings. That way, the opposed sheets or foils of lithium lock to each other through the perforations. The anode 14 has an extended tab or lead 15 (FIGS. 3 to 5) of the same metal as the anode current collector, i.e., preferably stainless-steel, that is contacted by a weld to the conductive cell casing 18 in a case-negative configuration. If desired, instead of one elongate tab 15, there can be multiple tabs spaced along the upper edge of the anode current collector.

The separator 40 provides physical separation between the anode 14 and the cathode 16. The separator 40 is typically of several sheets that are formed into an envelope that houses the cathode 16. The separator 40 is of an electrically insulative material to prevent an internal electrical short circuit between the electrodes, and the separator material also is chemically unreactive with the anode active material and cathode material and both chemically unreactive with and insoluble in the catholyte. In addition, the separator has a degree of porosity sufficient to allow flow therethrough of the catholyte during the electrochemical reactions of the cell.

Illustrative separator materials include non-woven glass, polypropylene, polyethylene, microporous material, glass fiber materials, ceramics, polytetrafluorethylene membrane commercially available under the designations ZITEX (Chemplast Inc.), polypropylene membrane, commercially available under the designation CELGARD (Celanese Plastic Company Inc.) and DEXIGLAS (C. H. Dexter, Div., Dexter Corp.). Other separator materials that are useful with the present invention include woven fabric separators comprising halogenated polymeric fibers, as described in U.S. Pat. No. 5,415,959 to Pyszczek et al., which is assigned to the assignee of the present invention and incorporated herein by reference. Examples of halogenated polymeric materials suitable for the lithium oxyhalide electrochemical cell of the present invention include, but are not limited to, polyethylene tetrafluoroethylene which is commercially available under the name Tefzel, a trademark of the DuPont Company; polyethylenechlorotrifluoroethylene which is commercially available under the name Halar, a trademark of the Allied Chemical Company, and polyvinylidene fluoride.

The cathode 16 is comprised of two sheets of a cathode material that are electrochemically non-active, but electrically conductive. Preferred electrochemically non-active but electrically conductive carbonaceous cathode materials include acetylene black, graphitic and non-graphitic forms of carbon, coke, charcoal, and combinations thereof.

In addition, a binder material such as a powdered fluoropolymer, more preferably powdered polytetrafluoroethylene (PTFE) or powdered polyvinylidene fluoride (PVDF), is typically added to the cathode material. The binder may comprise from about 1 to about 15 weight percent of the cathode material.

The cathode 16 for incorporation into the present lithium oxyhalide electrochemical cell 10 is typically prepared by rolling, spreading, pressing or otherwise contacting a cathode mixture of the electrochemically non-active but electrically conductive carbonaceous cathode material and the binder onto a suitable current collector selected from the group of stainless-steel, nickel, titanium, tantalum, platinum, gold, aluminum, cobalt nickel alloys, nickel-containing alloys, highly alloyed ferritic stainless-steel containing molybdenum and chromium, nickel-, chromium- and molybdenum-containing alloys, conductive carbon, and conductive polymers. The cathode current collector is preferably a stainless-steel screen having a plurality of perforations or openings. That way, opposed sheets of the cathode mixture lock to each other through the perforations in the cathode current collector.

In addition to the lithium anode and the cathode composed of the electrochemically non-active but electrically conductive carbonaceous material, lithium oxyhalide cells of the present invention comprise a catholyte that is typically composed of an electrochemically active cathode material that also serves as the liquid electrolyte. In that respect, the catholyte serves as a medium for migration of ions between the anode and the cathode during the cell's electrochemical reactions. In a preferred embodiment, the catholyte comprises a nonaqueous solvent depolarizer. Suitable nonaqueous solvent depolarizers exhibit those physical properties necessary for ionic transport, namely, low viscosity, low surface tension and wettability. The nonaqueous solvent depolarizer may be one or a mixture of more than one of the inorganic solvents which can serve as both a solvent and a depolarizer such as thionyl chloride, sulfuryl chloride, selenium oxychloride, chromyl chloride, phosphoryl chloride, phosphorous sulfur trichloride, and mixtures thereof. Thionyl chloride and sulfuryl chloride are two commonly used catholytes.

The ionic conductivity of the nonaqueous catholyte solution is preferably facilitated by a dissolved lithium salt. Exemplary salts are lithium halides such as LiCl and LiBr and those of the $LiMX_n$ type, such as $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiN(SO_2CF_3)_2$, LiSCN, $LiO_3SCF_2CF_3$, $LiC_6F_5SO_3$, $LiO_2$, $LiO_2CCF_3$, $LiSO_3F$, $LiB(C_6H_5)_4$, $LiCF_3SO_3$, and mixtures thereof. Suitable salt concentrations typically range between about 0.25 to about 2.0 molar. The solution of the nonaqueous solvent depolarizer and the ionic salt serves as the co-depolarizer and catholyte of the oxyhalide cell.

As an electrochemically non-active but electrically conductive material, the carbonaceous cathode 16 provides a surface on which reaction products from a reduction reaction between lithium ions from the anode 14 and active cathode constituents from the catholyte deposit. During cell discharge, a reduction reaction occurs between lithium and the oxyhalide catholyte. The reduction reaction produces a discharge voltage and lithiated chloride that deposits on the cathode surface and within pores of the carbonaceous cathode material. Discharge of the lithium oxyhalide cell continues until either of the anode or catholyte materials are exhausted, or the surface area of the carbonaceous cathode 16 becomes occupied with reaction products, thereby causing the reduction reaction to cease.

Because the catholyte provides both the electrochemically active cathode material and the electrolyte in a lithium oxyhalide cell, the cell volume is generally efficiently utilized. In comparison to primary cells of other chemistries, lithium oxyhalide cells typically have energy densities on the order of about 700 Wh/L to about 1200 Wh/L. The generally high energy densities and the ability of such cells to operate under extreme temperature conditions make lithium oxyhalide electrochemical cells ideally suited to power a wide range of devices used in extreme environments such as downhole drilling and testing applications that require a long discharge life.

As shown in FIG. 2, the anode 14, which is at least two times as long as the cathode 16, is folded so that a first elongate anode inner portion 14A faces an inner major side or surface of the cathode 16 and a second elongate anode outer potion 14B faces an outer major side or surface of the cathode. The anode inner and outer portions 14A, 14B are connected to each other by a U-shaped anode connecting portion 14C. This construction provides anode material facing the entire extent of the spaced-apart or opposed major surfaces of the cathode 16 with the anode inner portion 14A directly facing the cathode first side, the anode outer portion 14B directly facing the cathode second side, and the anode connecting portion 14C facing a cathode proximal end 16A. The side-by-side anode 14 and cathode 16 are then rolled into the wound-shaped electrode assembly 12 illustrated in FIGS. 2 to 4.

FIG. 2 further shows that in cross-section there is an imaginary anode reference radius "A" radiating outwardly from a center point 42 at the center of the wound-shaped electrode assembly 12. It is understood that the center point 42 is one of an infinite number of center points along a central axis of the wound-shaped electrode assembly 12. Each of the infinite number of center points has an anode reference radius A radiating outwardly therefrom.

With the anode inner and outer portions 14A, 14B rolled with the cathode 16 into the illustrated wound-shape, the anode reference radius A extending from the center point 42 intersects the curved U-shaped anode connection portion 14C at a tangent point indicated by numerical designation 44. The rolled anode inner and outer portions 14A, 14B make one complete 360° rotation around the center point 42 from the tangent point 44 to intersect the imaginary anode reference radius A at respective anode inner and outer locations indicated with numerical designations 46 and 48. However, the anode 16 does not make a second 360° rotation about the center point 42. Instead, the anode inner portion 14A ends from about 350° to about 20° short of the imaginary anode reference radius A. The anode outer portion 14B ends closer to the imaginary anode reference radius A but is still from about 340° to about 10° short of that radius. This means that the anode outer portion 14B is somewhat longer than the anode inner portion 14A, which ensures that both major surfaces of the cathode 16 are opposed by lithium.

FIG. 2 is also provided with an imaginary cathode reference radius "C" extending outwardly from the center point 42. As previously described with respect to the anode reference radius A, the center point 42 is one of an infinite number of center points along a central axis of the wound-shaped electrode assembly 12, each center point having a cathode reference radius C radiating outwardly therefrom.

The cathode reference radius C extends from the center point 42 and is coincident with the inner-most cathode proximal end 16A. The wound cathode 16 makes one complete 360° rotation around the center point 42 from the coincident cathode proximal end 16A to cross the imaginary cathode radius C at a cathode intersection location indicated with numerical designation 50. However, in a similar manner as with the anode 14, this drawing shows that the wound cathode 16 does not make a second 360° rotation around the center point 42. Instead, the outer-most cathode distal end 16B ends from about 345° to about 15° short of the imaginary cathode reference radius C.

Thus, one key difference of the present lithium oxyhalide electrochemical cell in comparison to a conventional spirally-wound lithium oxyhalide cell is that instead of a single layer of each of the anode and cathode rolled together into a jelly-roll or spirally-wound configuration, the electrode assembly 12 of the present invention has only one layer of anode 14 provided in two portions 14A and 14B that face the opposed major surfaces of the cathode 16. This is referred to as an inner anode portion/cathode/outer anode portion wound-shaped electrode assembly 12. Even in the outermost wrap, there is no section of the intermediate cathode 16 that is not facing a correctly-balanced portion of the anode 14. There is, therefore, no need for the outermost section of the anode to be reduced in thickness to ensure that the electrodes are balanced as previously described for a conventional spirally-wound design. Both of the anode inner and outer portions 14A, 14B connected by the anode connecting portion 14C and the cathode 16 are of a constant thickness along their entire lengths. That the anode 14 and cathode 16 are of a uniform thickness ensures that current density is uniform along the electrodes, and this, in turn, ensures that the overall discharge efficiency is maximized. In addition, the uniform thickness of the anode 14 and cathode 16 greatly simplifies the construction of the electrodes themselves, as well as the processes that are required for placing the electrode assembly 12 into the cell casing 18.

Further, the present lithium oxyhalide electrochemical cell includes features that strengthen the structural integrity of the electrode assembly 12. As in the previously described conventional moderate-rate cell design, the present electrode assembly 12 uses the same elongate tab or tabs 15 along the top of the anode 14 so that the anode is securely welded to the cylindrically-shaped casing sidewall 24 along substantially the entire inner circumference thereof. Also, because the wound electrode assembly 12 does not extend into a full multiple-layer spiral, there is a sufficiently large central hole to receive a spring 52 (FIG. 2) therein. The spring 52 is preferably a sheet of stainless-steel that is wound into a cylinder and inserted into the center hole of the electrode assembly 12. The spring 52 presses outwardly against the anode 14 and the cathode 16 to help maintain firm outward pressure or bias on the electrode assembly 12 against the inner surface of the casing sidewall 24. This helps immobilize the electrodes in a way that is not possible in a conventional spirally-wound structure.

In downhole drilling and testing applications there is a need for high-rate lithium oxyhalide electrochemical cells in which the magnetic signature of the cells is less than 40 nanoTesla (nT). To achieve this low value of magnetic induction or magneticflux density, it is necessary to use non-active materials with very low magnetic signatures. Conventional lithium oxyhalide electrochemical cells typically use some nickel components. That is the anode and cathode current collectors as well as the anode current collector tab 15 connected to the casing 18 and the cathode current collector tab 17 (FIGS. 4 and 5) connected to the terminal pin 32 in the glass-to-metal seal 30 are typically made of nickel. However, in the present lithium oxyhalide cells where a very low magnetic signature is required, the nickel components are replaced with similar components made of stainless-steel (either 304 or 316L). The electrical conductivity of stainless-steel is about one tenth that of nickel. Unfortunately, this lower conductivity can limit the overall rate capability of the cell in certain cases.

To help ameliorate this lower conductivity, one embodiment of the lithium oxyhalide electrochemical cells of the present invention uses stainless-steel for both the anode and cathode current collectors as well as the anode current collector tab 15 that is electrically connected to the cylindrical container 20 of the casing 18. However, an exemplary embodiment of the present invention uses nickel for the cathode current collector tab 17 connected to the positive terminal pin 32 to provide the cell 10 with very high-rate capability while maintaining the cell's magnetic signature at values less than 10 nT, which is well below the requirement of <40 nT. Otherwise, if a low magnetic signature is not desired, another exemplary embodiment of the present lithium oxyhalide electrochemical cells has stainless-steel anode and cathode current collectors as well as stainless-steel for both the anode and cathode current collector tabs 15 and 17.

Another component that plays a role in the discharge performance of lithium oxyhalide electrochemical cells according to the present invention is the lithium salt that provides the catholyte with its ionic conductivity. There are two lithium salts that are typically used in lithium-thionyl chloride cells: lithium tetrachloroaluminate ($LiAlCl_4$) and lithium tetrachlorogallate ($LiGaCl_4$). Catholytes containing the gallium-based salt ($LiGaCl_4$) generally show less voltage delay when the cells are first started up, and they usually give higher capacity when the cells are discharged under constant current conditions. In side-by-side comparison tests, however, it has been found that the aluminum-based salt ($LiAlCl_4$) shows less voltage drop when high-current pulses are applied during testing under certain defined pulsed-discharge conditions. When catholytes using only the aluminum-based or the gallium-based salt are used, the capacities that are obtained depend strongly on the cut-off voltage as measured during the highest-current pulse. Catholytes containing gallium-based salts give relatively higher overall capacity to a cut-off voltage of about 2.0 V. However, catholytes having aluminum-based salts give much higher pulse voltages and, as a result, remained above a 2.5 V cut-off much longer than lithium oxyhalide cells having catholytes with gallium-based salts. According to the present invention, the best performance is obtained with a catholyte containing a mixture of the lithium tetrachloroaluminate ($LiAlCl_4$) and lithium tetrachlorogallate ($LiGaCl_4$) salts. The salts are present in preferred molar ratios ranging from about 1:10 $LiAlCl_4$: $LiGaCl_4$ to about 10:1 $LiAlCl_4$: $LiGaCl_4$.

Under most pulse voltage conditions this mixed-salt catholyte gives the highest capacity whether taken to a cut-off of about 2.5 V or about 2.0 V. Thus, this mixed-salt catholyte is optimal for providing very high discharge capacity under pulsed-discharge conditions-higher than catholytes containing either the aluminum-based salt or the gallium-based salt alone.

The preferred form of the lithium oxyhalide electrochemical cell of the present invention is a case-negative design. In a case-negative design, the fabricated anode 14, cathode 16 and intermediate separator 40 are rolled together into the electrode assembly 12 shown in the cross-section of FIG. 2 such that the cathode 16 resides intermediate the outer anode portion 14A and the inner anode portion 14B. The electrode assembly 12 is inserted into the conductive metal casing 18 and the stainless-steel anode current collector tab or tabs 15 are connected to the casing 18 or lid 22, or to both, as is well known to those skilled in the art. A preferred material for the casing 18 is stainless-steel, although titanium, mild steel, nickel, nickel-plated mild steel and aluminum are also suitable.

The glass-to-metal seal 30 preferably comprises a corrosion resistant glass 34 having from between about 0% to about 50% by weight silica, such as CABAL 12, TA 23 or FUSITE MSG-12, FUSITE A-485, FUSITE 425 or FUSITE 435. The positive terminal pin 32 preferably comprises stainless-steel such as 52-alloy or 446 stainless-steel, although titanium, molybdenum and aluminum can also be used. The nickel or stainless-steel cathode lead 17, as the case may be, is welded to the positive terminal pin 32 in the glass-to-metal seal 30 and the lid 22 is welded to the casing 18 containing the electrode assembly 12. The casing 18 is thereafter filled with the catholyte described hereinabove through the fill port 36 and hermetically sealed such as by close-welding a stainless-steel ball 38 into the fill port, but not limited thereto.

As is well known to those skilled in the art, however, the exemplary electrochemical system of the present invention can also be constructed in a case-positive configuration. That is where the anode current collector tab 15 is connected to the terminal pin 32 and the cathode current collector tab 17 is connected to the casing 18/lid 22.

The electrochemical cell 10 of the present invention operates in the following manner. When the ionically conductive catholyte solution becomes operatively associated with the anode 14 and the cathode 16, an electrical potential difference is developed between terminals operatively connected to the anode and the cathode. During discharge, the electrochemical reaction at the anode includes oxidation of the lithium metal to form lithium ions. The electrochemical reaction at the cathode involves conversion of these ions which migrate from the anode to the cathode where they encounter chloride ions that are formed by reduction of the thionyl chloride or sulfuryl chloride depolarizer, and deposit onto the carbon surface as a lithium chloride salt. In addition, the halogen and/or interhalogen of the catholyte is believed to undergo a reaction or reactions with the lithium ions thereof, resulting in the formation of a compound or complex which exhibits the observed open circuit voltage of the cell.

It is appreciated that various modifications to the inventive concepts described herein may be apparent to those skilled in the art without departing from the spirit and scope of the present invention as defined by the hereinafter appended claims.

What is claimed is:
1. An electrochemical cell, comprising:
   a) a casing; and
   b) a wound-shaped electrode assembly housed inside the casing, the wound-shaped electrode assembly comprising:
      i) an anode comprising:
         A) an anode current collector having opposed anode current collector major sides; and
         B) an anode having a proximal U-shaped anode connecting portion connected to an anode inner portion extending to an anode inner portion distal end, and connected to an anode outer portion extending to an anode outer portion distal end, wherein the anode current collector has an anode active material contacted to its opposed major sides extending from the anode inner portion distal end, through the proximal U-shaped anode connecting portion, and to the anode outer portion distal end;
      ii) a cathode comprising:
         A) a cathode current collector having opposed cathode current collector first and second major sides; and

B) a cathode material contacted to the opposed first and second major sides of the cathode current collector so that the cathode has opposed cathode first and second major sides extending from a cathode proximal end to a cathode distal end;

iii) a separator disposed intermediate the U-shaped anode and the cathode to prevent direct physical contact between them; and iv) a catholyte in electrochemical association with the U-shaped anode and the cathode, v) wherein, in the wound-shaped electrode assembly, the proximal U-shaped anode connecting portion directly faces the cathode proximal end, the anode inner portion directly faces the cathode first major side, and the anode outer portion directly faces the cathode second major side with the anode inner and outer portions residing side-by-side from adjacent to the proximal end of the anode outer portion to the anode inner portion distal end and with the anode inner and outer portions facing the opposed cathode first and second major sides in a first 360° rotation about a center point of the wound-shaped electrode assembly and continuing in a second rotation about the center point with a distal segment of the anode outer portion extending outwardly for a greater distance beyond the distal ends of both the anode inner portion and the cathode so that the distal segment of the anode outer portion is in a direct facing relationship with the anode outer portion residing in the first 360° rotation without there being any segment of the anode inner portion and the cathode between the direct facing relationship of the distal segment of the anode outer portion in the second rotation and the anode outer portion in the first 360° rotation.

2. The electrochemical cell of claim 1, wherein a spring resides inside the wound-shaped electrode assembly to apply a biasing force against the electrode assembly with the anode outer portion contacting an inner surface of the casing.

3. The electrochemical cell of claim 2, wherein the spring is of stainless-steel.

4. The electrochemical cell of claim 1, wherein:

i) the casing supports a glass-to-metal seal comprising a terminal pin surrounded by a sealing glass;

ii) the anode comprises lithium contacted to the opposed major sides of the anode current collector comprising stainless-steel having at least one stainless-steel anode current collector tab electrically connected to the casing; and iii) the cathode comprises cathode material contacted to the opposed major sides of the cathode current collector comprising stainless-steel having a nickel cathode current collector tab connected to the terminal pin of the glass-to-metal seal supported by the casing.

5. The electrochemical cell of claim 4, wherein the casing comprises an open-ended container closed by a lid, and the container and lid are of stainless-steel, and wherein the cell has a magnetic flux density that is less than 10 nT.

6. The electrochemical cell of claim 1, wherein:

i) the casing supports a glass-to-metal seal comprising a terminal pin surrounded by a sealing glass;

ii) the anode comprises lithium contacted to the opposed major sides of the anode current collector comprising stainless-steel having at least one stainless-steel anode current collector tab electrically connected to the casing; and iii) the cathode comprises cathode material contacted to the opposed major sides of the cathode current collector comprising stainless-steel having a stainless-steel cathode current collector tab connected to the terminal pin of the glass-to-metal seal supported by the casing.

7. The electrochemical cell of claim 1, wherein the catholyte comprises a nonaqueous depolarizer selected from the group of thionyl chloride, sulfuryl chloride, selenium oxychloride, chromyl chloride, phosphoryl chloride, phosphorous sulfur trichloride, and mixtures thereof.

8. The electrochemical cell of claim 1, wherein the catholyte includes a salt selected from LiCl, LiBr, $LiPF_6$, $LiBF_4$, $LiAsF_6$, $LiSbF_6$, $LiClO_4$, $LiAlCl_4$, $LiGaCl_4$, $LiC(SO_2CF_3)_3$, $LiN(SO_2CF_3)_2$, LiSCN, $LiO_3SCF_2CF_3$, $LiC_6F_5SO_3$, $LiO_2$, $LiO_2CCF_3$, $LiSO_3F$, $LiB(C_6H_5)_4$, $LiCF_3SO_3$, and mixtures thereof.

9. The electrochemical cell of claim 1, wherein the catholyte comprises either thionyl chloride or sulfuryl chloride containing a mixture of $LiAlCl_4$ and $LiGaCl_4$ dissolved therein.

10. The electrochemical cell of claim 9, wherein the salts are present in the catholyte in molar ratios ranging from about 1:10 $LiAlCl_4$: $LiGaCl_4$ to about 10:1 $LiAlCl_4$: $LiGaCl_4$.

11. The electrochemical cell of claim 1, wherein the cathode comprises the cathode material mixed with a binder selected from powdered polytetrafluoroethylene and powdered polyvinylidene fluoride.

12. The electrochemical cell of claim 1, wherein the cathode material is an electrochemically non-active but electrically conductive carbonaceous cathode material selected from acetylene black, graphitic, carbon, coke, charcoal, and combinations thereof.

13. The electrochemical cell of claim 1, wherein the separator is in the form of an envelope containing the cathode.

14. The electrochemical cell of claim 1, wherein, with the wound-shaped electrode assembly encircling the center point of the electrode assembly, a) an imaginary cathode reference radius extending outwardly from the center point is coincident with the cathode proximal end and intersects the cathode at a cathode intersection location intermediate the cathode proximal and distal ends; and b) an imaginary anode reference radius extending outwardly from the center point intersects the proximal U-shaped anode connecting portion at a tangent point and then intersects the anode inner and outer portions at respective anode inner and outer intersection locations intermediate the proximal U-shaped anode connecting portion and the respective anode inner and outer portion distal ends.

15. The electrochemical cell of claim 14, wherein, after intersecting the cathode at the cathode intersection location, the imaginary cathode reference radius does not further intersect the cathode.

16. The electrochemical cell of claim 14, wherein, after intersecting the anode inner and outer portions at the respective anode inner and outer intersection locations, the imaginary anode reference radius does not further intersect the anode.

17. The electrochemical cell of claim 14, wherein:

i) the anode inner portion distal end ends from about 350° to about 20° from the imaginary anode reference radius;

ii) the anode outer portion distal end ends from about 340° to about 10° from the imaginary anode reference radius; and iii) the cathode distal end ends from about 345° to about 15° from the imaginary cathode reference radius.

18. An electrochemical cell, comprising:
a) a cylindrically-shaped casing; and
b) a wound-shaped electrode assembly housed inside the cylindrically-shaped casing, the wound-shaped electrode assembly comprising:
   i) an anode current collector having opposed anode current collector major sides; and
   B) lithium contacted to the opposed major sides of the anode current collector, the U-shaped anode having a proximal U-shaped anode connecting portion connected to an anode inner portion extending to an anode inner portion distal end, and connected to an anode outer portion extending to an anode outer portion distal end, wherein the lithium contacted to the opposed major sides of the anode current collector extends from the anode inner portion distal end, through the proximal U-shaped anode connecting portion, and to the anode outer portion distal end;
   ii) a cathode comprising:
   A) a cathode current collector having opposed first and second cathode current collector major sides; and
   B) acetylene black contacted to the opposed first and second major sides of the cathode current collector so that the cathode has opposed cathode first and second major sides extending from a cathode proximal end to a cathode distal end;
   iii) a separator disposed intermediate the U-shaped anode and the cathode to prevent direct physical contact between them; and
   iv) a catholyte in electrochemical association with the U-shaped anode and the cathode, wherein the catholyte comprises either thionyl chloride or sulfuryl chloride containing a mixture of $LiAlCl_4$ and $LiGaCl_4$ dissolved therein,
   v) wherein, in the wound-shaped electrode assembly, the proximal U-shaped anode connecting portion directly faces the cathode proximal end, the anode inner portion directly faces the cathode first major side, and the anode outer portion directly faces the cathode second major side with the anode inner and outer portions residing side-by-side from adjacent to the proximal end of the anode outer portion to the anode inner portion distal end and with the anode inner and outer portions facing the opposed cathode first and second major sides in a first 360° rotation about a center point of the wound-shaped electrode assembly and continuing in a second rotation about the center point with a distal segment of the anode outer portion extending outwardly for a greater distance beyond the distal ends of both the anode inner portion and the cathode so that the distal segment of the anode outer portion is in a direct facing relationship with the anode outer portion residing in the first 360° rotation without there being any segment of the anode inner portion and the cathode between the direct facing relationship of the distal segment of the anode outer portion in the second rotation and the anode outer portion in the first 360° rotation.

19. The electrochemical cell of claim 18, wherein:
   i) the cylindrically-shaped casing comprises an open-ended stainless-steel container closed by a stainless-steel lid, the cylindrically-shaped casing supporting a glass-to-metal seal comprising a terminal pin surrounded by a sealing glass;
   ii) the lithium of the anode is contacted to the opposed major sides of the anode current collector comprising stainless-steel having at least one stainless-steel anode current collector tab electrically connected to the cylindrically-shaped casing; and
   iii) the acetylene black of the cathode is contacted to the opposed major sides of the cathode current collector comprising stainless-steel having a nickel cathode current collector tab connected to the terminal pin of the glass-to-metal seal supported by the cylindrically-shaped casing.

20. The electrochemical cell of claim 18, wherein the cell has a magnetic flux density that is less than 10 nT.

21. The electrochemical cell of claim 18, wherein, with the wound-shaped electrode assembly encircling the center point of the electrode assembly,
   a) an imaginary cathode reference radius extending outwardly from the center point is coincident with the cathode proximal end and intersects the cathode at a cathode intersection location intermediate the cathode proximal and distal ends; and
   b) an imaginary anode reference radius extending outwardly from the center point intersects the proximal U-shaped anode connecting portion at a tangent point and then intersects the anode inner and outer portions at respective anode inner and outer intersection locations intermediate the proximal U-shaped anode connecting portion and the respective anode inner and outer portion distal ends.

22. An electrochemical cell, comprising:
a) a cylindrically-shaped casing;
b) a glass-to-metal seal supported by the cylindrically-shaped casing, the glass-to-metal seal comprising a terminal pin surrounded by a sealing glass; and
c) a wound-shaped electrode assembly housed inside the cylindrically-shaped casing, the wound-shaped electrode assembly comprising:
   i) a U-shaped anode comprising:
   A) a stainless-steel anode current collector having opposed anode current collector major sides; and
   B) lithium contacted to the opposed major sides of the stainless-steel anode current collector having at least one stainless-steel anode current collector tab electrically connected to the cylindrically-shaped casing, the U-shaped anode having a proximal U-shaped anode connecting portion connected to an anode inner portion extending to an anode inner portion distal end, and connected to an anode outer portion extending to an anode outer portion distal end, wherein the lithium contacted to the opposed major sides of the anode current collector extends from the anode inner portion distal end, through the proximal U-shaped anode connecting portion, and to the anode outer portion distal end;
   ii) a cathode comprising:
   A) a stainless-steel cathode current collector having opposed cathode current collector first and second major sides; and
   B) cathode material contacted to the opposed first and second major sides of the stainless-steel cathode current collector having a nickel cathode current collector tab connected to the terminal pin of the glass-to-metal seal supported by the cylindrically-shaped casing, wherein the cathode has opposed cathode first and second major sides extending from a cathode proximal end to a cathode distal end;

iii) a separator disposed intermediate the U-shaped anode and the cathode to prevent direct physical contact between them; and iv) a catholyte in electrochemical association with the U-shaped anode and the cathode, v) wherein, in the wound-shaped electrode assembly, the proximal U-shaped anode connecting portion directly faces the cathode proximal end, the anode inner portion directly faces the cathode first major side, and the anode outer portion directly faces the cathode second major side with the anode inner and outer portions residing side-by-side from adjacent to the proximal end of the anode outer portion to the anode inner portion distal end and with the anode inner and outer portions facing the opposed cathode first and second major sides in a first 360° rotation about a center point of the wound-shaped electrode assembly and continuing in a second rotation about the center point with a distal segment of the anode outer portion extending outwardly for a greater distance beyond the distal ends of both the anode inner portion and the cathode so that the distal segment of the anode outer portion is in a direct facing relationship with the anode outer portion residing in the first 360° rotation without there being any segment of the anode inner portion and the cathode between the direct facing relationship of the distal segment of the anode outer portion in the second rotation and the anode outer portion in the first 360° rotation.

* * * * *